United States Patent [19]

Koyama et al.

[11] Patent Number: 5,130,126
[45] Date of Patent: Jul. 14, 1992

[54] POLYMER-DRUG CONJUGATE AND A METHOD OF PRODUCING IT

[75] Inventors: Yoshiyuki Koyama, Noda; Shuji Kojima, Kashiwa; Tsuyoshi Miyazaki, Tsukuba; Akinori Suginaka, Chigasaki; Takeo Matsumoto; Yoshishige Murata, both of Tsukuba, all of Japan

[73] Assignee: Nippon Oil & Fats Co., Ltd., Tokyo, Japan

[21] Appl. No.: 676,384

[22] Filed: Mar. 28, 1991

[30] Foreign Application Priority Data

Jul. 9, 1990 [JP] Japan .................................. 2-179691

[51] Int. Cl.⁵ .................... A61K 31/74; A61K 31/52; A61K 31/557
[52] U.S. Cl. .................................. 424/78.18; 514/34; 514/42; 514/50; 514/261; 514/370; 514/396; 514/729; 514/925
[58] Field of Search ......................................... 424/78

[56] References Cited

PUBLICATIONS

Abuchowski et al. (1984), Cancer Biochem. Biophys., vol. 7, pp. 175-186.
Katre et al. (1987), Proc. Natl. Acad. Sci. USA, vol. 84, pp. 1487-1491.
Chemical Abstracts 96(8): 57661c, (1981).
Chemical Abstracts 108(26: 226780q, (1987).
Chemical Abstracts 111(24): 219277q, (1989).

*Primary Examiner*—Thurman K. Page
*Assistant Examiner*—Raj Bawa
*Attorney, Agent, or Firm*—Antonelli, Terry, Stout & Kraus

[57] ABSTRACT

The present invention provides a polymer-combined drug having directional characteristics to digestive organs, wherein it comprises a medicine combined with a polymer which has an alkyleneoxy group as a repeating unit. The polymer-combined drug is produced by reacting a polyoxyalkylene glycol having one or more terminal functional groups and a medicine, if necessary in a solvent, and if necessary in the presence of a catalyst. It is able to administer the drug orally or by intravenous injection so as to maintain the concentration in blood stably for a long time, and to absorb or take in digestive organs such as the stomach and intestines directly.

3 Claims, No Drawings

POLYMER-DRUG CONJUGATE AND A METHOD OF PRODUCING IT

BACKGROUND OF THE INVENTION

The present invention relates to a polymer-combined drug having directional characteristics to digestive organs by which the drug is specifically carried into digestive organs, particularly the stomach or intestines, and to a method for producing the drug.

Hitherto, for carrying medicines having directional characteristics to the stomach or intestines, drugs such as an oral drug and a suppository should be administered to the internal organs directly or adjacently. When a medicine is administered intravenously, since the blood concentration is increased rapidly, the secondary effect of the medicine causes trouble. Further, since the medicine is excreted rapidly, there are problems such as low durability of the effect of the medicine and the like.

In polyalkyleneoxy compounds, particularly polyethylene glycol has low toxicity and non-immunogenicity. It is known widely that the compound administered orally or intravenously is little harmful for the human body. However, the movement of these compounds in the body after medication is little reported, and it is reported only that the compounds are rapidly excreted after intravenous injections.

In general, it is said that water-soluble materials having relatively high molecular weight are bad for permeability to a mucosa and they are little absorbed (M. D. Donovan et al, Pharmaceutical Res., Vol. 7, 863 (1990)).

As a mucosa of the digestive tract prevents absorption of water-soluble medicines which are orally administered, it is a serious obstacle to take effect by using various water-soluble medicines, such as ionic cholinolytics and peptide medicines.

SUMMARY OF THE INVENTION

The present invention aims to solve the above problems and to provide a polymer-combined drug having directional characteristics to digestive organs by which a medicine, for example a therapeutic drug or a diagnostic drug, is administered by an intravenous injection so that it can be specifically carried into digestive organs comprising sublingual systems, especially the stomach and intestines, and by which it is specifically and efficiently absorbed from the stomach and intestines by oral administration.

The inventors of the present invention have found that a compound combined with a medicine and a polymer having an alkyleneoxy group, such as polyethylene glycol and the like, as a principal repeating unit shows the following polymer effects by the polymerization of the medicine itself:

(1) the secondary effect and the like are diminished by avoidance of undesirable accumulation of the medicine into the internal organs, tissues and the like, and (2) the effect of the medicine are maintained by delay of excretion, and it has the following characteristics which is not realized by known medicines and carriers:

(3) the compound has a property of very high directional characteristics to the stomach and intestines, (4) the compound is permeable into gastric mucosa to be secreted into the stomach, (5) the stomach acts as a reservoir of the medicine, and (6) the compound is rapidly absorbed by oral administration into the intestines and it is efficiently absorbed from the stomach by passing rapidly through a gastric mucosal barrier. Then, the present invention has been completed, Namely, the present invention provides a polymer-combined drug having directional characteristics to digestive organs, characterized in that it comprises a medicine combined with a polymer which has an alkyleneoxy group as a repeating unit. Further, the present invention is a method for producing the polymer combined drug, comprising reacting a polyoxy alkylene glycol having one or more terminal functional groups and a medicine, if necessary in the presence of a catalyst and in a solvent.

The following description illustrates the present invention more specifically.

As the polymer having an alkyleneoxy group as a repeating unit, polyethylene glycol, polypropylene oxides, polybutylene oxides, ethylene oxide-propylene oxide copolymers, polymers obtained by substituting the terminal groups of the above polymers with an acyl, amino or allyl group, and copolymers of the above polymers and acrylic acid, maleic acid, styrene or the like are preferably exemplified. The molecular weight of the above polymer is 100–200,000, preferably 800–100,000.

The above-mentioned polymers having desired molecular weight can be obtained by addition polymerization of ethylene oxide, propylene oxide or the like by using a well-known method.

From these polymers, the drugs having directional characteristics to digestive organs are obtained by binding medicines such as a therapeutic drug and a diagnostic drug.

It is enough to use any compound as the therapeutic drug, preferably drugs which take effect directly on diseases of digestive organs, particularly the stomach and bowels. As drugs for peptic ulcer, pipethamate ethobromide, oxapium iodide, propantheline bromide, methylbenactyzium bromide, chloropapaverine, brimamide, metiamide, cimetidine, urogastrone, sulpiride, nitric sulfate aluminum, gefarnate and the like can be exemplified. As therapeutic drugs for ulcerative colitis, salazosulfapyridine and the like can be exemplified.

Besides, brimamide, metiamide, cimetidine, ranitidine, nizatidine, famotidine, loxachidine and nizatidine as $H_2$-blockers, pirenzepine and terenzepine as M1-blockers, proglumide, CR-501 and antigastrin as gastrin receptor-blockers, alsalmin, azulene, alginates, aceglutamide aluminium, aldioxa, troxipide, L-glutamine, methyl methionine sulfonium chloride, teblenone, clepoplide maleate, cetraxate, spizofulon and irsogradine maleate as protective factor augmentors, ornoprostil, misoprostol, rioprostil, enprostil, rosaprostilarbaprostil, trimoprostil, $PGE_1$, $PGE_2$ and dimethyl $PGE_2$ as PG derivatives, atropine, scopolia extract, dicyclomine, oxyphencyclimine, pipethanate, etomidoline, butylscopolamine bromide and butolopium bromide as cholinolytic drugs and the like can be exemplified.

Since the polymer materials can maintain high concentration in blood, the binding to generalized drugs is effective. As the generalized drugs, bleomycin, adreamicin, mytomycin, KF-118, 5-fluorouracil derivatives, and 6-mercaptopurine derivatives which are anticancer, and several prostaglandin pharmaceuticals are exemplified.

As the diagnostic drugs, radioisotopelabeled polymers having an alkyleneoxy group as a principal repeating unit can be used. To obtain the polymers, a method for $^{125}$I labeling a polymer by chloramine T or glucose oxidase, a method for $^{125}$I labeling a polymer after tyrosine is introduced into the polymer, a method for bonding covalently a $^{125}$I labeled compound or metal chelate to a polymer and the like can be used.

Further, any methods for combining medicines with the above polymers including covalent bond, ionic bond, coordinate bond, Schiff base formation and the like can be used and the most suitable method can be selected according to each medicine. Then, functional groups required to carry the medicine in the polymer is preferably introduced into the polymer. The following methods are exemplified;

1) a method for reacting PGE, in which a terminal carboxy group is introduced, with a medicine having an amino group and/or a hydroxyl group and/or thiol group in the molecule, 2) a method for reacting PGE, in which an amino group and/or a hydroxyl group and/or a thiol group at the terminal is introduced, with the above medicine, 3) a method for reacting a copolymer, which is obtained from PGE having a terminal allyl group and carboxylic acid anhydride to have an carboxyl group, with the above medicine.

In these reactions, triethylamine, pyridine, sodium hydroxide, potassium hydroxide, sodium carbonate, potassium carbonate and N, N'-dicyclohexyl carbodiimide, as a catalyst or a condensation agent, and activated esterification agents such as succinimides and nitrophenol can be used. When necessary, water, benzene, toluene, ether, acetone, ethyl acetate, dimethylformamide, dimethyl sulfoxide and the like can be used as a solvent. The reaction temperatures are $-10°$ C. to $+200°$ C., preferably $0°$ to $120°$ C., and the reaction times are one minute to 170 hours, preferably 10 minutes to 24 hours.

The polymer-combined drug of the present invention can be formed into various forms. For example, tablets, powder, granules, aqueous solutions, suspensions, emulsions, capsules, medicinal oil, ointment and suppositories are preferred. The polymer-combined drug of the present invention can be administered by injection, oral, sublingual administration or suppository and the dosage can be determined optionally within the limits of conventional use.

When the polymer-combined drug of the present invention which has directional characteristics to digestive organs is used, therapeutic drugs or diagnostic drugs can be selectively carried by an intravenous injection into digestive organs such as the stomach and intestines. Accordingly, the greatest effect of the therapeutic drugs or diagnostic drugs is provided in the digestive organs, and the secondary effect can be diminished in the other internal organs.

When the polymer-combined drug of the present invention is administered orally or by a suppository from the rectum, the concentration in blood can be stably maintained for a long time in comparison with conventional methods, and the polymer-combined drug can be absorbed or taken in digestive organs such as the stomach and intestines directly and efficiently.

Concerning the drugs for targeting the stomach, particularly, since it is directly absorbed from the stomach, adsorption and decomposition in the liver which are problems in the absorption through the small intestines can be avoided.

Further, according to the method of the present invention, the aimed polymer-combined drug can be obtained certainly and efficiently.

DESCRIPTION OF PREFERRED EMBODIMENTS

The following examples illustrate the present invention more specifically.

EXAMPLE 1

Polyethylene glycol derivative (molecular weight 5100) having a terminal amino group was N-acylated with o-acetyloxybenzoyl chloride in benzene in the presence of triethylamine. The PEG-aspirin combined compound which was obtained in the above was $^{125}$I-labeled by a conventional chloramine T method and the product was purified with Sephadex G-25 (manufactured by Pharmacia Fine Chemical Company). Then, molecular weight cut-off was conducted with an ultrafiltration device to obtain a polymer sample having a molecular weight of about 5,400.

0.5% phosphoric acid buffer physiologic saline of the polymer obtained was prepared and 0.2 ml of the solution was intravenously injected in a mouse tail (about 20 g of body-weight).

After a certain time, the mouse was killed in a syncopic state to take out the internal organs, and the accumulation of the polymer in each organ was examined with a $\gamma$-counter. The results are shown in Table 1.

As shown in Table 1, the polymer is specifically accumulated in large quantities in the stomach and the greater part moved to the stomach contents. Further, in the case of a mouse of which pylorus was ligated high radio activity was also observed in the stomach contents. Accordingly, it seems the polymer was secreted out of the stomach. Moreover, the polymer accumulated in the small intestines 3–4 times as much as in muscles.

TABLE 1

Movement of the polyethylene glycol derivative (molecular weight: 5400) in the mouse body after the intravenous injection in the tail

| | Healthy mouse 2 h (n = 5) | (%-dose/g) Pylorus-ligated mouse 2 h (n = 2) |
|---|---|---|
| Blood | 1.201 | 1.301 |
| Liver | 0.450 | 0.702 |
| Kidney | 1.730 | 2.510 |
| Stomach | 5.210 | 5.450 |
| Stomach contents | 8.246 | 5.4 |
| Small intestine | 0.330 | — |

EXAMPLE 2

The same procedure as in Example 1 was repeated except that polyethylene glycol having a molecular weight of about 100,000 was used to examine the movement in the mouse body. The results are shown in Table 2.

TABLE 2

Movement of the polyethylene glycol derivative (molecular weight: 100,000) in the mouse body after the intravenous injection in the tail

| | (%-dose/g) Healthy mouse 2 h (n = 5) |
|---|---|
| Blood | 60.275 |
| Liver | 1.022 |

TABLE 2-continued

Movement of the polyethylene glycol derivative (molecular weight: 100,000) in the mouse body after the intravenous injection in the tail

|  | (%-dose/g) Healthy mouse 2 h (n = 5) |
| --- | --- |
| Kidney | 0.501 |
| Stomach | 3.045 |
| Small intestine | 0.905 |

EXAMPLE 3

The same procedures as in Example 1 was repeated except that polyethylene glycol having a molecular weight of about 50,000 was used to examine the movement in the mouse body. The results are shown in Table 3.

TABLE 3

Movement of the polyethylene glycol derivative (molecular weight: 50,000) in the mouse body after the intravenous injection in the tail

|  | (%-dose/g) Healthy mouse 2 h (n = 5) |
| --- | --- |
| Blood | 50.268 |
| Liver | 0.975 |
| Kidney | 1.942 |
| Stomach | 1.951 |
| Small intestine | 0.912 |

EXAMPLE 4

500 mg of an alternating copolymer of polyethylene glycol having a terminal allyl group and maleic anhydride was dissolved in 60 ml of DMSO. 500 mg of 6-mercaptopurine which is an anticancer agent and 250 μl of triethylamine were added to the solution and the mixture was reacted for 12 hours at room temperature. After the reaction was finished, 1 ml of water and 1 ml of triethylamine were added into the reactant and the mixture was left for one hour. Then, the polymer obtained was precipitated from ether-acetone (9:1), the precipitate was washed with ether and dried under reduced pressure. The polymer was dissolved in 20 ml of water, purified with Sephadex G-25 (manufactured by Pharmacia Fine Chemical Company) and lyophilized (yield: 290 mg).

The polymer obtained contained 15% by weight of 6-mercaptopurine. The polymer was $^{125}$I-labeled by a chloramine T method, the polymer labeled was intravenously injected into a mouse tail. After two hours, the mouse was killed in a syncopic state, and the accumulation of the polymer carrying 6-mercaptopurine in each organ was examined with a γ-counter. The results are shown in Table 4.

TABLE 4

Movement of the polyethylene glycol carrying 6-mercaptopurine in the mouse body after the intravenous injection in the tail (n = 1)

|  | (%-dose/g) |
| --- | --- |
| Blood | 8.983 |
| Liver | 2.244 |
| Kidney | 2.866 |
| Stomach | 6.542 |
| Small intestine | 1.557 |

EXAMPLE 5

Polyethylene glycol derivative (molecular weight 5100) having a terminal amino group was N-acylated with o-acetyloxybenzoyl chloride in benzene in the presence of triethylamine. The PEG-aspirin combined compound which was obtained in the above was $^{125}$I-labeled by a conventional chloramine T method and the product was purified with Sephadex G-25. Then, molecular weight cut-off was conducted with an ultrafiltration device to obtain a polymer sample having a molecular weight of about 5,400.

0.5% phosphoric acid buffer physiologic saline of the polymer (5 μg/ml) obtained was prepared and 0.2 ml of the solution was orally administered to a mouse (about 30 g of body-weight).

After a certain time, the mouse was killed in a syncopic state to take out the internal organs, and the accumulation of the polymer in each organ was examined with a γ-counter. The results are shown in Table 5.

As shown in Table 5, the polymer is rapidly absorbed and shows high concentration in blood. Further, it is shown that the polymer is found in tissues of the stomach and the small intestine in substantial quantity.

Moreover, surprisingly, the results of pylorus-ligated mouse show that the polymer is absorbed relatively rapidly in the stomach.

TABLE 5

Movement of the polyethylene glycol derivative (molecular weight: 5400) in the mouse body after the oral administration (%-dose/g)

|  | Healthy mouse 5 h (n = 5) | Pylorus-ligated mouse 2 h (n = 2) |
| --- | --- | --- |
| Blood | 1.517 | 0.300 |
| Liver | 0.939 | 0.659 |
| Kidney | 1.859 | 0.664 |
| Stomach | 18.457 | 11.062 |
| Small intestine | 1.220 | 0.607 |

EXAMPLE 6

The same procedure as in Example 5 was repeated except that polyethylene glycol having a molecular weight of about 100,000 was used to examine the movement in the mouse body. The results are shown in Table 6.

TABLE 6

Movement of the polyethylene glycol derivative (molecular weight: 100,000) in the mouse body after the oral administration (%-dose/g)

|  | Healthy mouse 5 h (n = 5) | Pylorus-ligated mouse 2 h (n = 2) |
| --- | --- | --- |
| Blood | 1.322 | 0.212 |
| Liver | 0.822 | 0.598 |
| Kidney | 0.608 | 0.398 |
| Stomach | 19.241 | 12.422 |
| Small intestine | 0.710 | 0.315 |

EXAMPLE 7

The same procedure as in Example 5 was repeated except that polyethylene glycol having a molecular weight of about 50,000 was used to examine the movement in the mouse body. The results are shown in Table 7.

TABLE 7

Movement of the polyethylene glycol derivative (molecular weight: 50,000) in the mouse body after the oral administration (%-dose/g)

|   | Healthy mouse 5 h (n = 5) | Pylorus-ligated mouse 2 h (n = 2) |
|---|---|---|
| Blood | 1.242 | 0.254 |
| Liver | 0.875 | 0.605 |
| Kidney | 0.795 | 0.488 |
| Stomach | 19.054 | 12.155 |
| Small intestine | 1.073 | 0.446 |

EXAMPLE 8

500 mg of an alternating copolymer of polyethylene glycol having a terminal allyl group and maleic anhydride was dissolved in 60 ml of DMSO. 500 mg of 6-mercaptopurine which is an anticancer agent and 250 μl of triethylamine were added to the solution and the mixture was reacted for 12 hours at room temperature. After the reaction was finished, 1 ml of water and 1 ml of triethylamine were added into the reactant and the mixture was left for one hour. Then, the polymer obtained was precipitated from ether-acetone (9:1), the precipitate was washed with ether and dried under reduced pressure. The polymer was dissolved in 20 ml of water, purified with Sephadex G-25 (manufactured by Pharmacia Fine Chemical Company) and lyophilized (yield: 290 mg).

The polymer obtained contained 15% by weight of 6-mercaptopurine. The polymer was 125I-labeled by a chloramine T method, 0.5 ml of a solution (600 μg/ml) of the polymer labeled was orally administered to a mouse. After two hours, the mouse was killed in a syncopic state, and the accumulation of the polymer carrying 6-mercaptopurine in each organ was examined with a γ-counter. The results are shown in Table 8.

TABLE 8

Movement of the polyethylene glycol carrying 6-mercaptopurine in the mouse body after the oral administration (n = 1) (%-dose/g)

| | |
|---|---|
| Blood | 0.800 |
| Liver | 1.204 |
| Kidney | 1.755 |
| Stomach | 38.397 |
| Small intestine | 1.243 |

EXAMPLE 9

One gramme of polyethylene glycol having terminal carboxyl groups (molecular weight: 3020) was dissolved in 14 ml of dry acetone. 137 mg of famotidine and 0.5 ml of dimethyl sulfoxide were added to the solution of dissolve thoroughly. Then, 0.24 ml of triethylamine and 162 mg of N-N'-dicyclohexyl carbodiimide were added to the solution in an ace bath, and the mixture was reacted at 5° C. for 12 hours. After the reaction was finished, the solvent was removed under reduced pressure. The residue was dissolved in a little water and the solution was gel-filtered with Sephadex G-25. The high molecular weight fraction was lyophilized to obtain a white spongy polymer-combined drug (yield: 974 mg). Famotidine contained in the drug was 3.8% by weight as a result of elemental analysis.

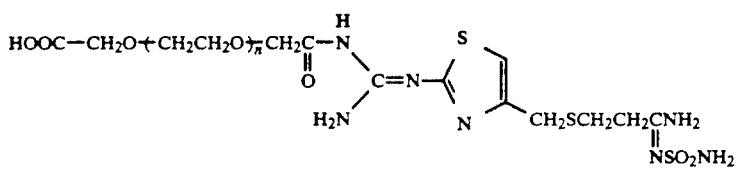

IR(KBr, cm$^{-1}$): 1700 (CO), 1300, 1150 (SO$_2$NH$_2$).
UV: $\lambda_{max}$305 nm.

EXAMPLE 10

402 mg of an alternating copolymer of polyethylene glycol having a terminal allyl group and maleic anhydride (molecular weight: 2000) was dissolved in 4 ml of dry acetone. 0.11 ml of triethylamine, 251 mg of famotidine and 2 ml of dimethyl sulfoxide were added to the solution, and the mixture was reacted at 5° C. for 12 hours. After the reaction was finished, the solvent was removed under reduced pressure. The residue was dissolved in a little water, the solution was purified with Sephadex G-25 and it was lyophilized to obtain a white solid polymer-combined drug (yield: 429 mg). Famotidine contained in the drug was 19.9% by weight as a result of elemental analysis.

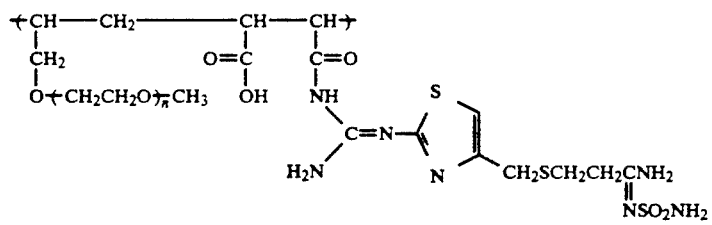

IR(KBr, cm$^{-1}$): 1700 (CO), 1300, 1150 (SO$_2$NH$_2$).

EXAMPLE 11

Synthesis of PGE Having a Terminal Group of Famotidine

Ten g of famotidne was dissolved in a mixture solvent of methylene chloride:dimethylsulfoxide (abbrevated as DMSO in the following)=1:1, 3.03 gramme of triethylamine was added to the solution and the mixture was stirred for 30 minutes. To the mixture, 20 ml of the above mixture solvent in which 4.5 g succinic anhydride was dissolved was added dropwise for 30 minutes, and the mixture obtained was stirred for 12 hours at room temperature. Then, the reaction mixture was poured into 100 ml of water, the precipitate obtained was recovered by centrifugation, washed repeatedly with water and freeze-dried to obtain 10.8 g (yield:82.6%) of a yellowish white powder. One g of the powder was dissolved in 5 ml of dimethylformamide (abbreviated as DMF in the following), 0.25 ml of triethylamine and 0.6 mg of N, N'-dicyclohexyl carbodiimide were added to the solution, and the mixture was stirred for 5 hours in ice cooling. To the mixture, 10 ml of a DMF solution in which 8.5 g of polyethylene glycol having a terminal amino group (MS=3360, manufactured by NIPPON OIL & FATS Co., LTD.) was dissolved was added dropwise for 30 minutes, and the mixture obtained was stirred for one hour in ice cooling. Further, the reaction mixture was stirred for 12 hours at room temperature and poured into 20 ml of water. After the precipitate was removed by centrifugation, the supernatant was filtered with a membrane filter having a hole diameter of 0.45 082 m and the filtrate was gel-filtered with a Sephadex G-25. The filtrate purified was freeze-dried and 7.2 g of white powder drug was obtained. Famotidine contained in the drug was 6.5% by weight from the result of a elemental analysis.

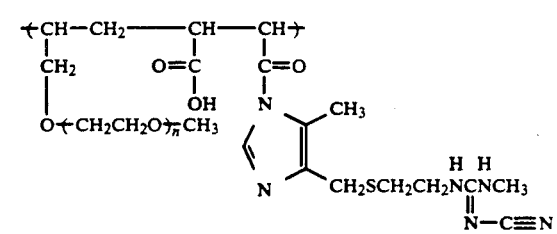

IR (KGr, cm$^{-1}$): 2250 (CN), 1670 (CON<), 1690 (COOH).

EXAMPLE 14

Using the polymer-combined drug obtained in Example 11, the inhibition of gastric secretion was determined by the following method.

Abdomen of a rat (six weeks, 159 g) was operated in urethane narcosis, a cannula was inserted in the pylorus. The stomach was washed three times with an isotonic sodium chloride solution and 3 ml of an isotonic sodium chloride solution was filled in the stomach. The solution

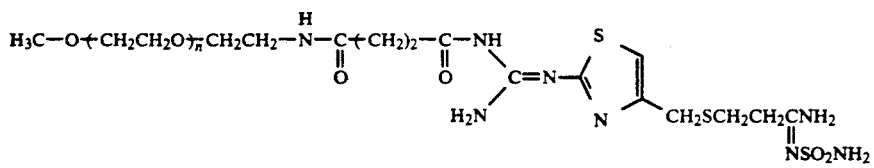

IR(KBr, cm$^{-1}$): 1700 (CO), 1300, 1150 (SO$_2$NH$_2$).
UV: $\lambda_{max}$ 305 nm.

EXAMPLE 12

The same procedure as in Example 11 was repeated except that cimetidine was used as a medicine to synthesize size a polymer-combined drug, 7.1 g of white powder was obtained. In the drug, the cimetidine content was 6.2% by weight as a result of elemental analysis.

was taken out after one hour and 3 ml of a new isotonic sodium chloride solution was filled in the stomach.

Histamine hydrochloride was intravenously injected into mouse tails in the ratio of 0.6 mg/animal every one hour, and after two hours, famotidine alone or the polymer-combined drug (famotidine content: 0.45 mg/animal) was intravenously injected.

3.5, 4 and 4.5 hours after the drugs were administered, the inhibition of gastric secretion was deter-

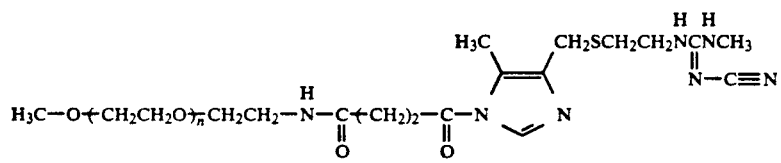

IR (KBr, cm$^{-1}$): 2250 (CN), 1670 (CON<), 1700 (CO).

EXAMPLE 13

The same procedure as in Example 10 was repeated except that cimetidine was used as a medicine to synthesize a polymer-combined drug. 544 mg of a white powder sample was obtained. In the drug, the cimetidine content was 18.8% by weight as a result of elemental analysis.

mined. The results are shown in Table 9.

TABLE 9

|  | 3.5 hours | 4.0 hours | 4.5 hours |
|---|---|---|---|
| Famotidine | 37% | 33% | 36% |
| Polymer drug | 46 | 61 | 53 |

Further, the intravenous injection method was changed to a direct administration method into the duodenum, and the inhibition of gastric secretion was determined. The results obtained in 1.5, 2.5 and 3.5 hours after the drugs were administered, are shown in Table 10.

TABLE 10

|  | 1.5 hours | 2.5 hours | 3.5 hours |
|---|---|---|---|
| Famotidine | 72% | 16% | 7% |
| Polymer drug | 37 | 36 | 31 |

As shown in the results, the effect of the polymer-combined drug is superior to that of famotidine alone with the exception of a part, and it is found that the polymer combined drug has durability.

EXAMPLE 15

The polymer-combined drug obtained in Example 13 was intravenously injected into mouse tails, the inhibition of gastric secretion was examined by the following method.

As soon as pylorus of a rat (150 mg) was ligated, an isotonic sodium chloride solution as a control, the polymer-combined drug obtained in Example 12 (cimetidine content: 0.4 mg) and 0.4 mg of cimetidine were administered, respectively, and then 0.6 mg of histamine hydrochloride was intravenously injected, the gastric juice was taken out after one hour, and content of acid was determined.

As a result, in comparison with the control, the inhibition effect of gastric secretion of cimetidine was 22%, and that of polymer-combined drug was 41%. Accordingly, it is found that the effect of the polymer-combined drug is superior to that of cimetidine alone, because the polymer-combined drug accumulates selectively in the stomach.

EXAMPLE 16

Using the polymer-combined drugs obtained in Examples 12 and 13, the inhibition of gastric secretion were determined by the following method.

Abdomen of male rats (180–240 g) were used after one night fasting. In urethane narcosis, cannulas for refluxing a liquid in the stomach were inserted and fixed in the pylorus and the cardiac orifice. A liquid for refluxing in the stomach was injected through the cardiac orifice canule by using a continuous injection pump (0.5 ml/minute), and the liquid was recovered through the pylorus canule.

Further, histamine hydrochloride (4.0 mg/kg/hour) was injected through the tail vein by using a continuous injection pump to stimulate the secretion of the gastric juice.

The reflux liquid flowing from the pylorus canule was recovered each 30 minutes and titrated with an automatic titrator until the pH value attained to 7.0, and the secretion quantity of the gastric juice was determined. The samples were intravenously administered in the tails each 1.5 hours after the injection of histamine hydrochloride was begun.

0.5, 1.5, 2.5, 3.5 and 4.5 hours after the samples of cimetidine, PEG-CIM 12 (exp. 12) and LPM-CIM 13 (Example 13) were administered, the inhibition of gastric secretion was determined. The results are shown in Table 11.

TABLE 11

|  | 0.5 | 1.5 | 2.5 | 3.5 | 4.5 | (hours) |
|---|---|---|---|---|---|---|
| Cimetidine | 30.7 | 28.6 | 32.4 | 21.1 | 24.4 | (%) |
| PEG-CIM 12 | 24.7 | 38.5 | 43.4 | 38.9 | 24.1 | |
| LPM-CIM 13 | 43.6 | 33.8 | 39.5 | 36.7 | 37.0 | |

In each case, 3.0 mg/kg of cimetidine content was intravenously injected.

EXAMPLE 17

Using the polymer-combined drugs obtained in Examples 9 and 10, the inhibition of gastric secretion was determined in the same method as shown in Example 15.

0.5, 1.5, 2.5, 3.5 and 4.5 hours after the samples of famotidine, PEG-FAM 9 which is a polymer-combined drug of famotidine (Example 9) and LPM-FAM 10 (Example 10) were administered, the inhibition of gastric secretion was determined. The results are shown in Table 12.

TABLE 12

|  | 0.5 | 1.5 | 2.5 | 3.5 | 4.5 | (hours) |
|---|---|---|---|---|---|---|
| Famotidine | 45.2 | 71.6 | 21.1 | −9.2 | −25.3 | (%) |
| PEG-FAM 9 | 40.0 | 72.6 | 34.8 | 30.6 | 4.6 | |
| LPM-FAM 10 | 48.9 | 73.9 | 50.9 | 42.0 | 15.6 | |

In each case, 0.1 mg/kg of famotidine content was intravenously injected.

As shown in the results of Examples 14–17, the effect of the polymer-combined drug is superior to that of cimetidine or famotidine alone, and it is found that the polymer-combined drug has durability, particularly in the case of the polymer-combined drug of famotidine, the durability is remarkably prolonged.

EXAMPLE 18

200 mg of PEG having a terminal methoxy group and a terminal amino group (MW =4300, manufactured by NIPPON OIL & FATS CO., LTD.) and 100 mg of chloromethylbenzoic acid were dissolved in 3 ml of methylene chloride. To the solution, N, N'-dicyclohexyl carbodiimide were added, and the mixture was stirred for 4 hours at room temperature and was permitted to stand for 12 hours. The reaction mixture was filtered, and the filtrate was concentrated under reduced pressure. The residue obtained was dissolved in 2 ml of water, the solution was gel-filtered with Sephadex G-25, and the polymer fraction was freeze-dried. White powder of PEG (PEG-CB) having a terminal chloromethylphenyl group was obtained. Water was separated as the benzene azeotrope from 20 mg of the powder obtained. Further the compound was dried in vacua in the presence of phosphorus pentaoxide and dissolved in 0.1 ml of dimethylformamide (A solution).

The other hand, 2 mg of 16, 16-dimethylprostaglandine $E_2$ was dissolved in 0.2 ml of a mixture solvent of ethanol:ethyl acetate=9:1, the solution was added to 4 ml of 50% of a cesium carbonate aqueous solution and the mixture was stirred for 30 minutes. The reactant was freeze-dried to obtain cesium 16, 16-dimethylprostaglandine. The whole of the compound was added to the above A solution, and the mixture was stirred for 18 hours at room temperature and concentrated under reduced pressure. Then, the residue was dissolved in 2 ml of water, and the solution was gel-filtered with Sephadex-25 to obtain a high molecular fraction. The fraction was freeze-dried and 20 mg of white powder of PEG-PG-A.

Further, from the difference of the absorbance at 270 nm between PEG-CM and PEG-PG, the content of 16, 16-dimethylprostaglandine $E_2$ in PEG-PG-A was 0.38 % by weight.

EXAMPLE 19

0.75 mg of PEG having a terminal methoxy group and a terminal amino group (MW =4300, manufactured by NIPPON OIL & FATS CO., LTD.), 0.5 mg of prostaglandin $E_2$, 0.16 mg of triethylamine and 20 mg of ethanol, and the carbodiimide were added in 0.5 ml of ethanol, and the mixture was stirred at room temperature for 18 hours and the reactant was concentrated under reduced pressure. The residue obtained was dissolved in 1 ml of water, the solution was gel-filtered with Sephadex G-25 to obtain a high molecular fraction, and the fraction was freeze-dried. 4.1 mg of white powder of PEG-PG-B was obtained. The content of prostaglandin $E_2$ was 0.22 % by weight.

EXAMPLE 20

0.5 mg of prostaglandin $E_1$ and 2.1 mg of N, N'-carbonyldiimidazole were added to 1 ml of dried tetrahydrofuran, and the mixture was stirred for 15 minutes at room temperature. To the mixture, 1 ml of a toluene solution of PEG (MW=4300, manufactured by NIPPON OIL & FATS CO., LTD.) having a terminal methoxy group and a terminal hydroxy group which was dried by azeotropic distillation (6.7 mg/ml) was added. The mixture was stirred for 72 hours at room temperature and the reactant was concentrated under reduced pressure. The residue was dissolved in 1 ml of water, the solution was gel-filtered with Sephadex G-25 to obtain a high molecular fraction, and the fraction was freeze-dried. 3.9 mg of white powder of PEG-PG-C was obtained. The content of prostaglandin $E_1$ was 0.33% by weight.

EXAMPLE 21

0.5 mg of 16, 16-dimethylprostaglandin $E_2$ and 2.1 mg of N, N'-carbonyldiimidazole were added to 1 ml of dried tetrahydrofuran, and the mixture was stirred for 15 minutes at room temperature. To the mixture, 1 ml of a toluene solution of PEG (MW=2000, manufactured by NIPPON OIL & FATS CO., LTD.) having two terminal hydroxy groups which was dried by azeotropic distillation (31.2 mg/ml) was added. The mixture was stirred for 72 hours at room temperature and the reactant was concentrated under reduced pressure. The residue was dissolved in 1 ml of water, the solution was gel-filtered with Sephadex G-25 to obtain a high molecular fraction, and the fraction was freeze-dried to obtain 29.1 mg of white powder of PEG-PG-D. The content of 16, 16-dimethylprostaglandin $E_2$ was 0.043 % by weight.

EXAMPLE 22

0.2 ml of a physiological sodium chloride solution as a control and 0.2 ml of a physiological sodium chloride solution of PEG-PG-A obtained in Example 18 (0.39 mg/ml) were orally administered to mice of 8 weeks (ddY, male, about 30 g, each n=3). After 30 minutes, 0.2 ml of pure ethanol was orally administered. After 50 minutes the mice were killed in a syncopic state and vivisected, and the damage of the stomach was examined. As a result, 5 to 7 spots of big hemorrhagic ulcer were observed in individuals of the control. However, one spot of small hemorrhage was observed in individuals of PEG-PG-A administration group.

EXAMPLE 23

The same procedure as in Example 22 was repeated except that a physiological sodium chloride solution of PEG-PG-D (2 mg/ml) obtained in Example 21 was used instead of PEG-PG-A, and the damage of the stomach was examined. As a result, 5 to 7 spots of big hemorrhagic ulcer were observed in individuals of the control. However, one spot of small hemorrhage was observed in individuals of the PEG-PG-D administration group.

EXAMPLE 24

0.2 ml of a physiological sodium chloride solution as a control and 0.2 ml of a physiological sodium chloride solution of PEG-PG-A obtained in Example 18 (39 ug/ml) were intravenously injected into mice tails of 8 weeks (ddY, male, about 30 g, each n=3). After 2 hours, 0.2 ml of pure ethanol was orally administered. After 50 minutes the mice were killed in a syncopic state and vivisected, and the damage of the stomach was examined. As a result, 5 to 7 spots of big hemorrhagic ulcer were observed in individuals of the control. However, zero or one spot of small hemorrhage was observed in individuals of the PEG-PG-A administration group.

EXAMPLE 25

0.2 ml of a physiological sodium chloride solution as a control and 0.2 ml of a physiological sodium chloride solution of PEG-PG-B obtained in Example 19 (68 µg/ml) were intravenously injected into mice tails of 8 weeks (ddY, male, about 30 g, each n=3). After 2 hours, 0.2 ml of pure ethanol was orally administered. After 50 minutes the mice were killed in a syncopic state and vivisected, and the damage of the stomach was examined. As a result, 5 to 7 spots of big hemorrhagic ulcer were observed in individuals of the control. However, zero or one spot of small hemorrhage was observed in individuals of the PEG-PG-B administration group.

EXAMPLE 26

0.2 ml of a physiological sodium chloride solution as a control and 0.2 ml of a physiological sodium chloride solution of PEG-PG-C obtained in Example 20 (45 µg/ml) were intravenously injected into mice tails of 8 weeks (ddY, male, about 30 g, each n=3). After 2 hours, 0.2 ml of pure ethanol was orally administered. After 50 minutes the mice were killed in a syncopic state and vivisected, and the damage of the stomach was examined. As a result, 5 to 7 spots of big hemorrhagic ulcer were observed in individuals of the control. However, one or two spots of small hemorrhage was observed in individuals of the PEG-PG-C administration group.

EXAMPLE 27

0.2 ml of a physiological sodium chloride solution as a control and 0.2 ml of a physiological sodium chloride solution of PEG-PG-D obtained in Example 21 (200 µg/ml) were intravenously injected into mice tails of 8 weeks (ddY, male, about 30 g, each n=3). After 2 hours, 0.2 ml of pure ethanol was orally administered. After 50 minutes the mouse was killed in a syncopic state and vivisected, and the damage of the stomach was examined. As a result, 5 to 7 spots of big hemorrhagic ulcer were observed in individuals of the control. However, one spot of small hemorrhage was observed in individuals of the PEG-PG-D administration group.

As shown in the results of Examples 22–27, the anti-ulcer effect of PEG-prostaglandin in the stomach was certainly acknowledged.

We claim:

1. A polymer-drug conjugate targeting the site of digestive organs, which comprises a medicine chemically bound to a polymer, said polymer having an alkyleneoxy group as a repeating unit and having a molecular weight of 800–100,000 and said medicine being selected from the group consisting of cimetidine, famotidine, mitomycin, adriamycin, 6-mercaptopurine, 5-fluorouracil, prostaglandin $E_1$, prostaglandin $E_2$ and dimethylprostagladin $E_2$.

2. A polymer-drug conjugate according to claim 1, wherein the alkyleneoxy group has a terminal carboxyl, hydroxyl, amino or allyl group.

3. A polymer-drug conjugate according to claim 1, wherein the polymer is a polyethyleneglycol.

* * * * *